United States Patent [19]

Murugesan et al.

[11] Patent Number: 4,855,480
[45] Date of Patent: Aug. 8, 1989

[54] BENZYLAMINOOXYMETHYL METHYLPROPANOIC ACID HERBICIDES

[75] Inventors: Natesan Murugesan, Lawrenceville; Mariano Guiducci, Edison, both of N.J.

[73] Assignee: FMC Corporation, Philadelphia, Pa.

[21] Appl. No.: 212,856

[22] Filed: Jun. 29, 1988

[51] Int. Cl.$^4$ .................... C07C 125/06; A01N 37/44
[52] U.S. Cl. ........................ 560/29; 562/434; 562/451; 560/20; 560/23; 71/107; 71/111
[58] Field of Search ............... 560/29, 20, 23; 71/107, 71/111

[56] References Cited

U.S. PATENT DOCUMENTS

| | | | |
|---|---|---|---|
| 3,649,664 | 3/1972 | Richler | 560/29 |
| 4,160,077 | 7/1979 | Brooks | 560/29 |
| 4,405,357 | 9/1983 | Chang | 71/88 |
| 4,552,585 | 11/1985 | Chang | 71/88 |
| 4,584,014 | 4/1986 | Patterson | 560/35 |
| 4,657,580 | 4/1987 | Krass | 560/35 |
| 4,692,182 | 9/1987 | Chang | 71/88 |

FOREIGN PATENT DOCUMENTS

| | | |
|---|---|---|
| 4075085 | 10/1985 | Australia . |
| 1567164 | 8/1969 | Fed. Rep. of Germany . |
| 1934227 | 1/1971 | Fed. Rep. of Germany . |
| 1430927 | 12/1963 | France . |
| 1126064 | 6/1986 | Japan . |
| 68/4280 | 11/1968 | South Africa . |

Primary Examiner—Paul J. Killos
Attorney, Agent, or Firm—Robert L. Andersen; H. Robin Ertelt

[57] ABSTRACT

Compounds of the formula

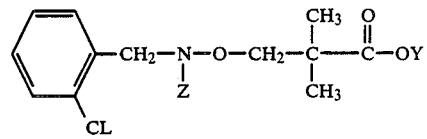

in which Y is hydrogen, lower alkyl, or an alkali metal or alkaline earth metal, and Z is selected from hydrogen, a hydrogen halide complex or a tri(lower)alkylmethoxycarbonyl group, their use as herbicides and herbicidal compositions thereof are disclosed.

4 Claims, No Drawings

BENZYLAMINOOXYMETHYL METHYLPROPANOIC ACID HERBICIDES

The present invention relates to derivatives of 2-(2-chlorobenzylaminooxymethyl)-2-methylpropanoic acid, compositions thereof, and their use as herbicides.

The herbicidal compounds of this invention are represented by the formula

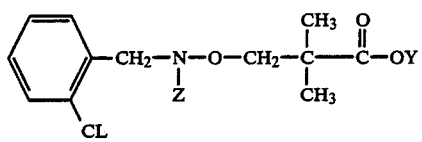

in which Y is hydrogen, lower alkyl, or an alkali metal or alkaline earth metal, and Z is selected from hydrogen, a hydrogen halide complex or a tri(lower)alkylmethoxycarbonyl group.

As used herein the term lower means 1–4 preferably one or two carbons and halo or halide refers to a halogen, preferably chlorine or bromine.

Specific examples are shown below.

| Compound No. | Y | Z |
|---|---|---|
| 1 | H | H |
| 2 | Na+ | H |
| 3 | H | C(O)OC(CH$_3$)$_3$ |
| 4 | CH$_3$ | H |
| 5 | C$_2$H$_5$ | H.HCL |

The foregoing compounds may be prepared as described in the examples below.

EXAMPLE 1

SYNTHESIS OF 2-(2-CHLOROBENZYLAMINOOXYMETHYL)-2-METHYLPROPANOIC ACID (COMPOUND 1)

Step A

Synthesis of 2-(2-chlorobenzylideneaminooxymethyl)-2-methylpropanoic acid

Concentrated sulfuric acid (4 mL) was added to a stirred mixture of 2-chlorobenzaldehyde (24.5 grams; 0.174 mole) and 4,4-dimethyl-3-isoxazolidinone (20.1 grams; 0.174 mole) in toluene (150 mL) cooled in an ice bath and under a nitrogen atmosphere. Upon completion of addition, the reaction mixture was stirred at ambient temperature overnight under a nitrogen atmosphere. The reaction mixture was then neutralized by the careful addition of solid sodium bicarbonate and then extracted with aqueous sodium bicarbonate (3×500 mL). The combined aqueous extracts were acidified to pH 3 with concentrated hydrochloric acid and then extracted with methylene chloride (3×150 mL). The dried (sodium sulfate) organic layer was concentrated under reduced pressure to afford 16 grams of 2-(2-chlorobenzylideneaminooxymethyl)-2-methylpropanoic acid as a solid, m.p. 78°–80° C.

Step B

Synthesis of 2-(2-chlorobenzylaminooxymethyl)-2-methylpropanoic acid

A solution of 2-(2-chlorobenzylideneaminooxymethyl)-2-methylpropanoic acid (6.38 grams; 0.025 mole) in 1:1 glacial acetic acid:ethanol (60 mL) was cooled to 0° C. (ice/salt bath) under a nitrogen atmosphere. Sodium cyanoborohydride (1.9 grams; 0.03 mole) was then added in five equal portions during a 20 minute period. The reaction mixture was then stirred for three days at ambient temperature under a nitrogen atmosphere. The reaction mixture was concentrated under reduced pressure to a volume of approximately 15 mL. This was poured into water (150 mL) and extracted twice with methylene chloride. The combined extracts were washed with water, dried (sodium sulfate), and concentrated under reduced pressure to afford a gum (7.2 grams). Product was purified by chromatography through silica gel, eluting with 5:1 methanol:methylene chloride. Appropriate fractions were combined and concentrated at reduced pressure to yield 2.9 grams of 2-(2-chlorobenzylaminooxymethyl)-2-methylpropanoic acid as a solid, m.p. 78°–80° C.

EXAMPLE 2

SYNTHESIS OF 2-(2-CHLOROBENZYLAMINOOXYMETHYL)-2-METHYLPROPANOIC ACID, SODIUM SALT (COMPOUND 2)

A mixture of 2-(2-chlorobenzylaminooxymethyl)-2-methylpropanoic acid (0.02 gram, 0.0008 mole) and aqueous sodium hydroxide (0.03 gram in 1 mL of water) was shaken for approximately ten minutes in a flask. Water was removed under reduced pressure. Diethyl ether (2 mL) was then added to the flask, the flask was shaken, and then the diethyl ether was carefully removed by pipet. The flask containing product was then placed in a dessicator for two hours to dry, yielding the sodium salt of 2-(2-chlorobenzylaminooxymethyl)-2-methylpropanoic acid as a solid.

EXAMPLE 3

SYNTHESIS OF 2-[N-(2-CHLOROBENZYL)-N-t-BUTOXYCARBONYLAMINOOXYMETHYL]-2-METHYLPROPANOIC ACID (COMPOUND 3)

Di-t-butyldicarbonate (8.0 grams, 0.04 mole) was added to a stirred solution of 2-(2-chlorobenzylaminooxymethyl)-2-methylpropanoic acid (8.0 grams, 0.03 mole) and sodium hydroxide (1.2 grams, 0.03 mole) in water (100 mL) at ambient temperature and under a nitrogen atmosphere. The reaction mixture was stirred overnight and then acidified to pH 5. This acidic mixture was extracted with methylene chloride (2×50 mL). The dried organic extract was then concentrated under reduced pressure to yield 12.5 grams of 2-[N-(2-chlorobenzyl)-N-t-butoxycarbonylaminooxymethyl]-2-methylpropanoic acid as a gum.

EXAMPLE 4

SYNTHESIS OF ETHYL 2-(2-CHLOROBENZYLAMINOOXYMETHYL)-2-METHYLPROPANOATE (COMPOUND 4)

Step A

Synthesis of 2-(2-Chlorobenzylideneaminooxymethyl)-2-methylpropanoic acid

The procedure was the same as Example 1, Step A, using 2-chlorobenzaldehyde (28.1 grams, 0.2 mole), and 4,4-dimethyl-3-isoxazolidinone (23 grams, 0.2 mole) to yield 17.3 grams of 2-(2-chlorobenzylideneaminooxymethyl)-2-methylpropanoic acid as a solid. Reaction was repeated.

Step B

Synthesis of Methyl 2-(2-chlorobenzylideneaminooxymethyl)-2-methylpropanoate

A solution of 2-(2-chlorobenzylideneaminooxymethyl)-2-methylpropanoic acid (31.6 grams; 0.12 mole) and concentrated sulfuric acid (2 mL) in methanol (100 mL) was heated at reflux for two hours and then stirred for 48 hours at ambient temperature. The reaction mixture was then heated for an additional four hours. The reaction mixture was concentrated under reduced pressure. Water (30 mL) and methylene chloride (30 mL) were added to the residue. The mixture was then neutralized with aqueous sodium carbonate and extracted with methylene chloride. The dried (magnesium sulfate) extract was concentrated under reduced pressure to yield 27.0 grams of methyl 2-(2-chlorobenzylideneaminooxymethyl)-2-methylpropanoate.

Step C

Synthesis of Methyl 2-(2-chlorobenzylaminooxymethyl)-2-methylpropanoate

A mixture of methyl 2-(2-chlorobenzylideneaminooxymethyl)-2-methylpropanoate (10.0 grams, 0.04 mole) and borane-pyridine complex (10.4 mL; 0.12 mole) in absolute ethanol (30 mL) was cooled in an ice bath. A solution of anhydrous 6.5N hydrogen chloride in ethanol (60 mL) was then added slowly. Upon completion of addition, the reaction mixture was stirred at ambient temperature for four hours. The reaction mixture was concentrated under reduced pressure, and methylene chloride (50 mL) was added to the residue. Aqueous sodium carbonate was then added to adjust the pH to 6–7. The layers were separated, and the organic layer was dried (magnesium sulfate) and concentrated under reduced pressure to yield a mixture of a white solid and liquid. The liquid was decanted off and purified by chromatography through silica gel, eluting successively with hexane and 20:1 hexane:ethyl acetate. Appropriate fractions were combined and concentrated at reduced pressure to yield 3.1 grams of methyl 2-(2-chlorobenzylaminooxymethyl)-2-methylpropanoate as a colorless liquid.

EXAMPLE 5

SYNTHESIS OF ETHYL 2-(2-CHLOROBENZYLAMINOOXYMETHYL) 2-METHYLPROPANOATE HYDROCHLORIDE (COMPOUND 5)

Dry hydrogen chloride gas was passed through a stirred solution of 2-(2-chlorobenzylaminooxymethyl)-2-methylpropanoic acid (2.0 grams; 0.01 mole) in absolute ethanol (100 mL) at ambient temperature for two minutes. The reaction mixture was stirred overnight under a nitrogen atmosphere. The reaction mixture was concentrated under reduced pressure. The residue was purified by passing it through a silica gel column, eluting first with methylene chloride (200 mL) and then with 95:5 methylene chloride:methanol. Appropriate fractions were combined and then concentrated under reduced pressure to afford 0.45 grams of ethyl 2-(2-chlorobenzylaminooxymethyl)-2-methylpropanoate hydrochloride as a colorless gum.

The compounds of the present invention were tested in preemergence and postemergence evaluations to assess their herbicidal activity.

The plant test species used in demonstrating the herbicidal activity of these compounds include cotton (*Gossypium hirsutum* var. Stoneville), soybean (*Glycine max* var. Williams), field corn (*Zea mays* var. Agway 425X), wheat (*Triticum aestivum* var. Prodax), field bindweed (*Convolvulus arvensis*), morningglory (*Ipomea lacunosa* or *Ipomea hederacea*), velvetleaf (*Abutilon theophrasti*), barnyardgrass (*Echinochloa crusgalli*), green foxtail (*Setaria viridis*), johnsongrass (*Sorghum halepense*), wild mustard (*Brassica kaber*), cutleaf nightshade (*Solanum triflorum*), hemp sesbania (*Sesbania exaltata*), sicklepod (*Cassia obtusifolia*), large crabgrass (*Digitaria sanguinalis*), proso millet (*Panicum miliaceum*), yellow nutsedge (*Cyperus esculentus*), rice (*Oryza sativa*), and lima bean (*Phaseolus limensis*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered and then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8–10 days after which the foliage of the emerged test plants was sprayed with a solution of the test compound in acetone-water containing up to 0.5% sorbitan monolaurate. After spraying, the foliage was kept dry for 24 hours and then watered regularly for 21 days after which phytotoxicity data were recorded.

Phytotoxicity data were taken as percent control or vigor/kill. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The following describes the values used in the two rating systems:

| Herbicide Rating System Using Percent Control | | | |
|---|---|---|---|
| Rating Percent Control | Description of Main Categories | Crop Description | Weed Description |
| 0 | No effect | No crop reduction | No weed control or injury |
| 10 | | Slight discoloration or stunting | Very poor weed control |
| 20 | Slight/effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate | Crop injury more lasting, recovery | Deficient to moderate weed |
| 60 | | Lasting crop injury no recovery | Moderate weed control |
| 70 | | Heavy injury and stand loss | Control somewhat less than satisfactory |
| 80 | Severe | Crop nearly destroyed a few survivors | Satisfactory to good weed control |
| 90 | | Only occasional live plants left | Very good to excellent control |

| | Herbicide Rating System Using Percent Kill and Vigor Ratings |
|---|---|
| 100 | Complete effect, Complete crop destruction, Complete weed destruction |
| 5 | Plants normal |
| 4 | Slight injury; plants will or have already recovered |
| 3 | Moderate injury; plants expected to recover |
| 2 | Moderate to severe injury; plants are not expected to recover |
| 1 | Severe injury; plants will not recover |
| 0 | Dead plant |

Representative test results are shown in Table I, using an application of 4 kg/ha unless otherwise noted.

PREMERGENCE TESTS
% Control (C) or Vigor/Kill (V K) (a)

| Compound No. | 1 | 2(a) | 3 | 4 | | 5 |
|---|---|---|---|---|---|---|
| | C | C | C | V | K | C |
| Cotton | 100 | 5 | 60 | 0 | 100 | — |
| Soybean | 0 | 5 | 0 | 5 | 0 | 10 |
| Corn | 80 | 0 | 95 | 0 | 100 | 100 |
| Rice | 5 | 20 | 30 | 3 | 0 | 95 |
| Wheat | 95 | 0 | 70 | 0 | 100 | 95 |
| Morningglory | 20 | 5 | 40 | — | — | 70 |
| Wild Mustard | 60 | 20 | 70 | — | — | 95 |
| Velvetleaf | 100 | 60 | 100 | 0 | 100 | 100 |
| Barnyardgrass | 80 | 50 | 100 | 0 | 100 | 100 |
| Green Foxtail | 80 | 10 | 95 | 3 | 95 | 100 |
| Johnsongrass | 40 | 0 | 80 | — | — | 100 |

POSTEMERGENCE TESTS

| Cotton | 50 | 30 | — | — | — | 50 |
|---|---|---|---|---|---|---|
| Soybean | 30 | 30 | — | — | — | 70 |
| Corn | 60 | 50 | — | — | — | 95 |
| Rice | 20 | 20 | — | — | — | 70 |
| Wheat | 70 | 60 | — | — | — | 70 |
| Morningglory | 20 | 30 | — | — | — | 100 |
| Wild Mustard | 70 | 70 | — | — | — | 80 |
| Velvetleaf | 60 | 70 | — | — | — | 90 |
| Barnyardgrass | 80 | 40 | — | — | — | 100 |
| Green Foxtail | 70 | 40 | — | — | — | 95 |
| Johnsongrass | 90 | 50 | — | — | — | 95 |

(a) 4 kg/ha application rate except for Compound No. 2 which was tested at 2 kg/ha.

In normal use the compounds of this invention are mixed for application with various agriculturally acceptable adjuvants, diluents, or carriers, and optionally other active ingredients to form herbicidal formulations which may be applied as such or further diluted for or during application. Thus, these compounds are suitable active ingredients for wettable powders, emulsifiable concentrates, water suspensions, flowable concentrates, dusts, powders, granules, and other formulations normally employed for agricultural applications.

The compounds thus prepared or diluted are then applied to the locus where control is desired, namely to the plant itself for postemergence applications or to the soil in which the plant or plant seed is or is about to be planted.

We claim:

1. A compound of the formula

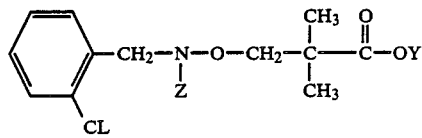

in which Y is hydrogen, lower alkyl or alkali metal or alkaline earth metal and Z is hydrogen, a hydrohalide complex or a tri(lower)alkylmethoxycarbonyl group.

2. A compound of claim 1 selected from the group consisting of
   (a) 2-(2-chlorobenzylaminooxymethyl)-2-methylpropanoic acid;
   (b) 2-(2-chlorobenzylaminooxymethyl)-2-methylpropanoic acid, sodium salt;
   (c) 2-[N-(2-chlorobenzyl)-N-t-butoxycarbonylaminooxymethyl]-2-methylpropanoic acid;
   (d) ethyl 2-(2-chlorobenzylaminooxymethyl)-2-methylpropanoate; and
   (e) ethyl 2-(2-chlorobenzylaminooxymethyl)-2-methylpropanoate hydrochloride.

3. An herbicidal composition comprising an herbicidally effective amount of a compound of claim 1 or 2 in admixture with an agriculturally acceptable adjuvant, diluent or carrier.

4. A method for controlling undesired vegetation comprising applying to the locus where control is desired an herbicidally effective amount of a compound of claim 1 or 2.

* * * * *